US011627996B2

(12) United States Patent
Jackson (10) Patent No.: US 11,627,996 B2
(45) Date of Patent: Apr. 18, 2023

(54) POLYAXIAL BONE SCREW WITH SPHERICAL CAPTURE, COMPRESSION INSERT AND ALIGNMENT AND RETENTION STRUCTURES

(71) Applicant: Roger P. Jackson, Praire Village, KS (US)

(72) Inventor: Roger P. Jackson, Praire Village, KS (US)

( * ) Notice: Subject to any disclaimer, the term of this patent is extended or adjusted under 35 U.S.C. 154(b) by 0 days.

(21) Appl. No.: 16/259,358

(22) Filed: Jan. 28, 2019

(65) Prior Publication Data

US 2019/0150988 A1  May 23, 2019

Related U.S. Application Data

(63) Continuation of application No. 15/009,062, filed on Jan. 28, 2016, now Pat. No. 10,231,757, which is a continuation of application No. 13/507,822, filed on Jul. 31, 2012, now Pat. No. 9,414,863, which is a continuation-in-part of application No. 12/924,260, filed on Sep. 23, 2010, now Pat. No. 8,403,962, and a continuation of application No. 12/072,354, filed on Feb. 26, 2008, now Pat. No. 10,076,361, and a continuation-in-part of application No. 12/008,067, filed on Jan. 8, 2008, now Pat. No. 7,901,437, application No. 12/924,260, which is a continuation-in-part of application No. 11/385,957, filed on Mar. 21, 2006, now abandoned, which is a continuation-in-part of application No. 11/178,854, filed on Jul. 11, 2005, now Pat. No. 7,789,896, application No. 13/507,822, which is a continuation-in-part of application No. 11/126,965, filed on May 10, 2005, now Pat. No. 7,476,239.

(60) Provisional application No. 60/905,472, filed on Mar. 7, 2007, provisional application No. 60/897,723, filed on Jan. 26, 2007, provisional application No. 60/655,239, filed on Feb. 22, 2005.

(51) Int. Cl.
*A61B 17/70* (2006.01)

(52) U.S. Cl.
CPC ...... *A61B 17/7035* (2013.01); *A61B 17/7037* (2013.01); *A61B 17/7032* (2013.01)

(58) Field of Classification Search
CPC .................................................. A61B 17/7037
See application file for complete search history.

(56) References Cited

U.S. PATENT DOCUMENTS

| 6,063,090 | A  | * | 5/2000 | Schlapfer | ........... | A61B 17/7037 606/270 |
| 6,280,442 | B1 | * | 8/2001 | Barker    | ............. | A61B 17/7037 606/256 |
| 6,869,433 | B2 |   | 3/2005 | Glascott  |             |                       |

(Continued)

*Primary Examiner* — Suba Ganesan
(74) *Attorney, Agent, or Firm* — Hoffman Warnick LLC (57) ABSTRACT

A polyaxial bone screw assembly includes a receiver, a shank, an articulation structure for retaining the shank in the receiver and a compression insert for engagement with a longitudinal connecting member such as a rod. The articulation structure includes substantially spherical convex and concave surfaces that slidably engage both shank and receiver surfaces to provide compound articulation between the receiver and the shank. The receiver includes inwardly directed spring tabs engaging the insert and prohibiting rotation of the insert within the receiver.

20 Claims, 9 Drawing Sheets

(56) References Cited

U.S. PATENT DOCUMENTS

| | | |
|---|---|---|
| 7,445,627 B2 | 11/2008 | Hawkes et al. |
| 9,414,863 B2 | 8/2016 | Jackson |
| 10,076,361 B2 | 9/2018 | Jackson |
| 2004/0138662 A1* | 7/2004 | Landry .............. A61B 17/7037 606/86 A |
| 2004/0193160 A1 | 9/2004 | Richelsoph |
| 2004/0267264 A1* | 12/2004 | Konieczynski .... A61B 17/7035 606/289 |
| 2005/0277928 A1 | 12/2005 | Boschert |
| 2006/0241600 A1* | 10/2006 | Ensign ................. A61B 17/704 81/52 |
| 2007/0049933 A1* | 3/2007 | Ahn ................... A61B 17/7037 606/279 |
| 2007/0118117 A1 | 5/2007 | Altarac et al. |
| 2007/0118123 A1* | 5/2007 | Strausbaugh ...... A61B 17/7049 606/272 |
| 2007/0270839 A1 | 11/2007 | Jeon et al. |
| 2016/0324543 A1 | 11/2016 | Jackson |
| 2018/0098797 A1 | 4/2018 | Jackson |

\* cited by examiner

POLYAXIAL BONE SCREW WITH SPHERICAL CAPTURE, COMPRESSION INSERT AND ALIGNMENT AND RETENTION STRUCTURES

CROSS REFERENCE TO RELATED APPLICATIONS

This application is a continuation of U.S. application Ser. No. 15/009,062 filed Jan. 28, 2016, which is a continuation of U.S. application Ser. No. 13/507,822, filed Jul. 31, 2012, now U.S. Pat. No. 9,414,863, which is a continuation of U.S. application Ser. No. 12/072,354 filed Feb. 26, 2008, now U.S. Pat. No. 10,076,361, which claims the benefit of U.S. Provisional Patent Application No. 60/905,472 filed Mar. 7, 2007, each of which is incorporated by reference in its entirety herein.

U.S. application Ser. No. 13/507,822 is also a continuation-in-part of U.S. application Ser. No. 12/008,067 filed Jan. 8, 2008, now U.S. Pat. No. 7,901,437, which claims the benefit of U.S. Provisional Patent Application No. 60/897,723 filed Jan. 26, 2007, each of which is incorporated by reference in its entirety herein.

U.S. application Ser. No. 13/507,822 is also a continuation-in-part of U.S. application Ser. No. 11/126,965 filed May 10, 2005, now U.S. Pat. No. 7,476,239, which is incorporated by reference in its entirety herein.

U.S. application Ser. No. 13/507,822 is also a continuation-in-part of U.S. application Ser. No. 12/924,260 filed Sep. 23, 2010, now U.S. Pat. No. 8,403,962, which is continuation-in-part of U.S. application Ser. No. 11/385,957 filed Mar. 21, 2006, now abandoned, which is a continuation-in-part of U.S. application Ser. No. 11/178,854 filed Jul. 11, 2005, now U.S. Pat. No. 7,789,896 which claims the benefit of U.S. Provisional Patent Application No. 60/655,239 filed Feb. 22, 2005, each of which is incorporated by reference in its entirety herein.

BACKGROUND OF THE INVENTION

The present invention is directed to polyaxial bone screws for use in bone surgery, particularly spinal surgery, and particularly to capture structures and inserts for such screws.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred.

Open-ended polyaxial bone screws allow rotation of the head or receiver about the shank until a desired rotational position of the head is achieved relative to the shank. Thereafter, a rod can be inserted into the head or receiver and eventually the receiver is locked or fixed in a particular position relative to the shank.

During the rod implantation process it is desirable to utilize bone screws or other bone anchors that have components that remain within the bone screw and further remain properly aligned during what is sometimes a very lengthy, difficult procedure. For example, some bone screws desirably include compression inserts or other parts that are designed to securely and fully engage surface portions of a rod or other longitudinal connecting member.

SUMMARY OF THE INVENTION

A polyaxial bone screw assembly according to the invention includes a shank having an upper portion and a body for fixation to a bone; a head or receiver defining an open channel; an articulation structure for retaining the shank upper portion within the receiver; and at least one compression insert. The articulation structure is disposed between the receiver and the shank upper portion and is slidingly mated to both the upper portion and the receiver, allowing for compound articulation of the shank with respect to the receiver. The receiver includes structure cooperating with the compression insert that retain such insert in a desired position and alignment within the receiver. Illustrated embodiments include spring tabs that project into the receiver cavity either upwardly or downwardly and into grooves or slots and/or flat surfaces formed in or on the insert.

OBJECTS AND ADVANTAGES OF THE INVENTION

Therefore, objects of the present invention include: providing an improved spinal implant assembly for implantation into vertebrae of a patient; providing such an assembly that includes an open longitudinal connecting member receiver, a shank pivotally connected to the rod receiving member, a rod or other longitudinal connecting member, and in some instances, an aligned pressure insert disposed between the shank and the rod; providing such an assembly that has a low profile after final installation; and providing such an assembly that is easy to use, especially adapted for the intended use thereof and wherein the implant assembly components are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-10, the reference numeral 1 generally designates a polyaxial bone screw assembly according to the present invention. The assembly 1 includes a shank 4 that further includes a body 6 integral with an upper portion or capture structure 8; a head or receiver 10; a retainer 12 illustrated as an open collar-like retaining and articulating structure; and a compression insert 14. The shank 4, head or receiver 10, retainer 12 and insert 14 are assembled prior to implantation of the shank body 6 into a vertebra 15.

Figure 1:
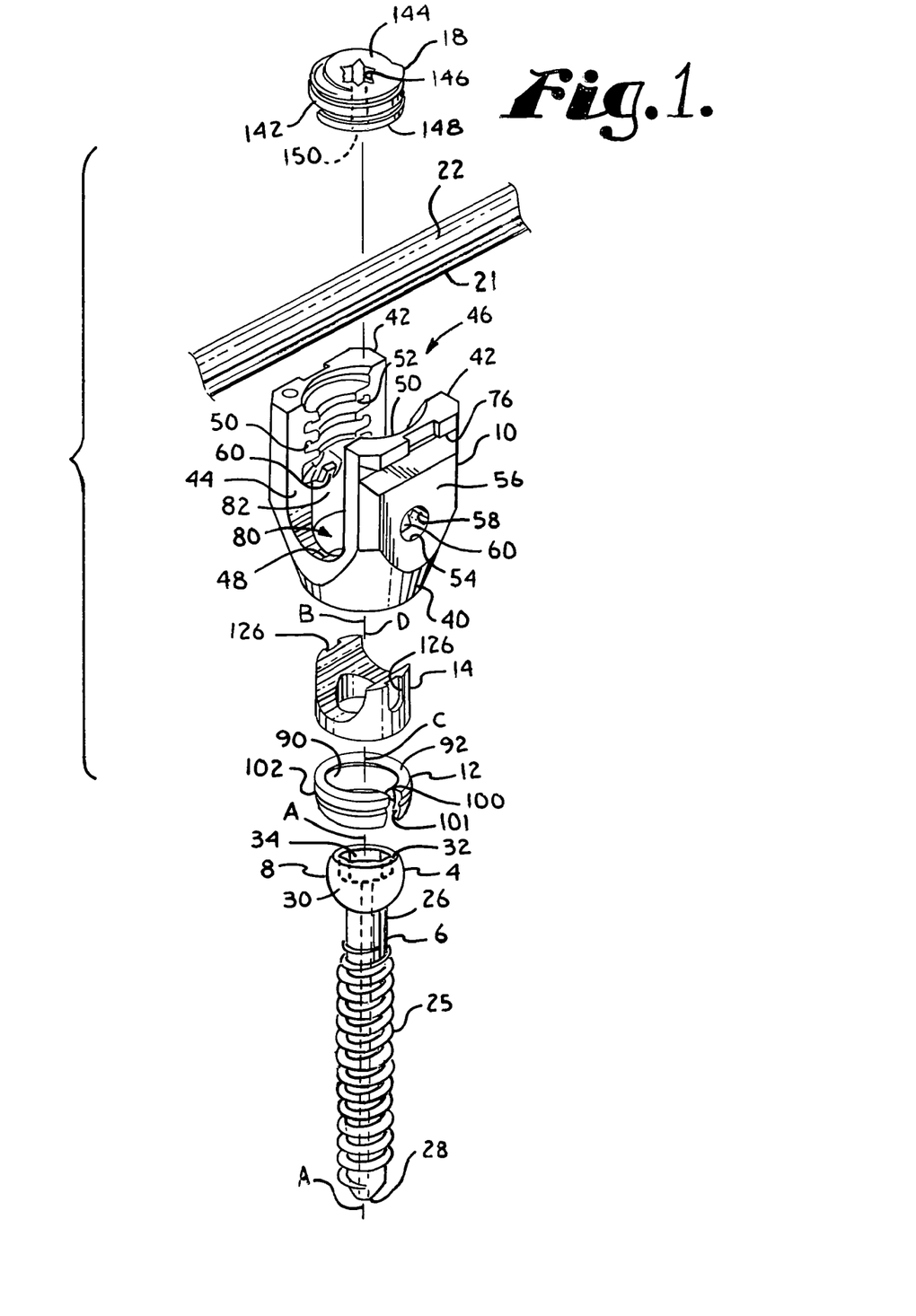
FIG. 1 is an enlarged exploded perspective view of a bone screw assembly according to the invention including a shank, a retainer, a compression insert and a receiver and shown with a cooperating longitudinal connecting member and a cooperating closure top.

FIG. 1 also shows a closure structure or top 18 for capturing a longitudinal connecting member within the head or receiver 10, such as a rod 21 having an outer cylindrical surface 22. Upon installation, which will be described in detail below, the closure top 18 presses against the rod 21 that in turn presses against the insert 14 that presses against the shank upper portion 8 which presses the retainer 12 into fixed frictional contact with the receiver 10, so as to fix the rod 21 relative to the bone screw 1 and thus to adjacent vertebrae. The receiver 10 and shank 4 cooperate in such a manner that the receiver 10 and shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other.

Figures 2, 3, 4:
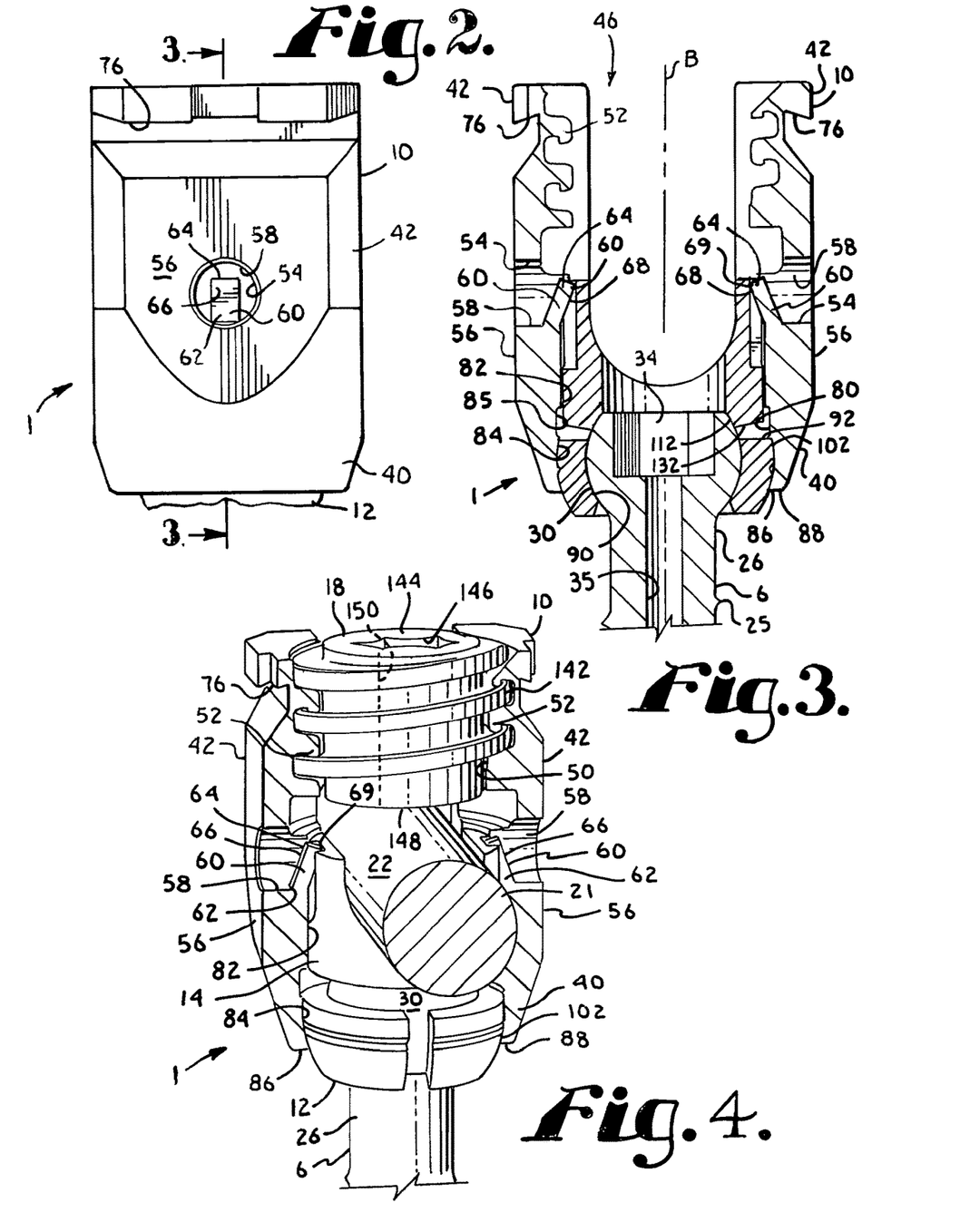
FIG. 2 is an enlarged and partial side elevational view of the bone screw assembly of FIG. 1.
FIG. 3 is an enlarged and partial cross-sectional view taken along the line 3-3 of FIG. 2.
FIG. 4 is an enlarged and partial perspective view of the bone screw assembly of FIG. 1 with portions broken away to show the detail thereof.

The bone screw shank 4, best illustrated in FIGS. 1 and 3, is elongate, with the shank body 6 having a helically wound bone implantable thread 25 extending from near a neck 26 located adjacent to the upper portion 8 to near a tip 28 of the body 6 and extending radially outwardly therefrom. During use, the body 6 utilizing the thread 25 for gripping and advancement is implanted into a vertebra (not shown) leading with the tip 28 and driven down into the vertebra with an installation or driving tool (not shown), so as to be implanted in the vertebra to near the neck 26. The shank 4 has an elongate axis of rotation generally identified by the reference letter A.

The neck 26 extends axially upwardly from the shank body 6. Further extending axially from the neck 26 is the shank upper portion or capture structure 8 that provides a connective or capture apparatus disposed at a distance from the thread 25 and thus at a distance from the vertebra (not shown) when the body 6 is implanted in such vertebra. The shank upper portion 8 is configured for connecting the shank 4 to the receiver 10 and capturing the shank 4 in the receiver 10. The shank upper portion 8 has an outer, convex and substantially spherical surface 30 that extends outwardly and upwardly from the neck 26 and terminates at a top 32. The illustrated top 32 is substantially planar and disposed perpendicular to the axis A. The spherical surface 30 has an outer radius configured for sliding cooperation and ultimate frictional mating with a concave surface of the retainer 12 that has a substantially similar radius. The spherical surface 30 is smooth, but it is foreseen that such surface may include a roughened or textured surface or surface finish, or may be scored, knurled, or the like, for enhancing frictional engagement with the retainer 12. A counter sunk drive feature 34 is formed in the top 32 (shown as a hexagonal aperture). In operation, a driving tool (not shown) engages the feature 34 for driving the shank body 6 into bone. The drive feature 34 may take a variety of tool-engaging forms and may include one or more apertures or imprints of various shapes, such as a pair of spaced apart apertures or a multi-lobular aperture, such as those sold under the trademark TORX, or the like. It is foreseen that in some embodiments, the bone screw shank upper portion may have an external tool engagement structure.

The illustrated shank 4 is cannulated, having a small central bore 35 extending an entire length of the shank 4 along the axis A, coaxial with the threaded body 6. The bore 35 has a first circular opening at the shank tip 28 and a second circular opening at the drive feature 34. The bore 35 provides a passage through the shank 4 interior for a length of wire (not shown) inserted into a vertebra (not shown) prior to the insertion of the shank body 6, the wire providing a guide for insertion of the shank body 6 into the vertebra.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2)$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With reference to FIGS. 1-4, the receiver 10 has a generally U-shaped appearance with a discontinuous partially cylindrical and partially spherical inner profile and a partially curved and partially faceted outer profile. The receiver has an axis of rotation B that is shown in FIG. 1 as being aligned with and the same as the axis of rotation A of the shank 4, such orientation being desirable during assembly of the receiver 10 with the shank 4, the retainer 12 and the insert 14. After the receiver 10 is pivotally attached to the shank 4, and the assembly 1 is implanted in a vertebra (not shown), the axis B is typically disposed at an angle with respect to the axis A.

The receiver 10 includes a base 40 integral with a pair of opposed upstanding arms 42 forming a cradle and defining a U-shaped channel 44 between the arms 42 with an upper opening 46 and a lower seat 48, the channel 44 having a width for receiving the rod 21, for operably snugly receiving the rod 21 between the arms 42. Each of the arms 42 has an interior surface 50 that defines the inner cylindrical profile and includes a partial helically wound guide and advancement structure 52. In the illustrated embodiment, the guide and advancement structure 52 is a partial helically wound interlocking flangeform configured to mate under rotation with a similar structure on the closure structure 18, as described more fully below. However, it is foreseen that the guide and advancement structure 52 could alternatively be a square-shaped thread, a buttress thread, a reverse angle thread or other thread like or non-thread like helically wound discontinuous advancement structure for operably guiding under rotation and advancing the closure structure 18 downward between the arms 42, as well as eventual torquing when the closure structure 18 abuts against the rod 21.

An opposed pair of tool receiving and engaging apertures 54 are formed on outer surfaces 56 of the arms 42. A pair of substantially cylindrical inner surfaces 58 define the apertures 54, with a portion of each of the apertures 54 extending through the arms 42 as best illustrated in FIG. 2. With particular reference to FIGS. 3 and 4, a pair of tabs 60, each having a lower end or body portion 62 integral with a respective arm 42 at a lower portion of one of the cylindrical surfaces 58, and an upper end 64 extending upwardly and inwardly from the respective lower body portion 62, the tab 60 generally directed towards the guide and advancement structure 52 of the respective arm 42 and also toward the axis B. As shown in FIGS. 1, 3 and 4, an operational orientation of each of the tabs 60 is angled toward the axis B with an inner surface 68 or edge 69 of the upper end 64 in sliding engagement with a slot in the cooperating insert 14 as will be described in greater detail below. The tabs 60 are typically initially disposed parallel to the axis B and then a tool (not shown) is inserted into the aperture 54 from the outside surface 56 and engages and pushes a surface 66 of the tab 60 and bends the tab 60 inwardly in a direction toward the axis B until the tab 60 is at the illustrated desired angular position. Such bending of the tabs 60 may be performed either prior to or after assembly of the receiver 10 with the insert 14, the shank 4 and the retainer 12. It is also foreseen that the tabs 60 may be machined or otherwise pre-fabricated to be angled or directed toward the axis B as is shown in the drawing figures. The illustrated tabs 60 are resilient, having a spring-like nature. Thus, when operatively cooperating with the insert 14, the tabs 60 bias against the insert 14, holding such insert in a desired position and yet the tabs 60 are flexible enough to allow a user to make desired adjustments of the position of the insert 14 within the receiver 10.

Each of the illustrated receiver arms 42 also includes a V-shaped or undercut tool engagement groove 76, formed on outer surfaces thereof which may be used for holding the receiver 10 with a holding tool (not shown) having projections that are received within the grooves 76 during implantation of the shank body 6 and/or during subsequent installation of the rod 21 or other longitudinal connecting member and the closure structure 18. It is foreseen that tool receiving grooves or apertures may be configured in a variety of shapes and sizes and be disposed at other locations on the receiver arms 42.

Communicating with the U-shaped channel 44 of the receiver 10 is a chamber or cavity 80 defined in part by a substantially cylindrical upper portion 82 and by a lower inner substantially spherical seating surface 84 of the base 40. The upper portion 82 is located below the guide and advancement structures 52 and may include one or more cylindrical surfaces for sliding cooperation with an insert or inserts. As illustrated in FIG. 3, the cylindrical upper portion 82 may include a lower section or portion 85 having a larger diameter than a remainder of the portion 82, the portion 85 located adjacent to the spherical seat 84 and providing clearance for movement of the retainer 12, including an expanding or spreading movement thereof during attachment with the shank upper portion 8 and for swiveling the retainer 12 to a desired orientation after assembly of the bone screw 1. The apertures 54 and the tabs 60 communicate with the cylindrical upper portion 82. The seating surface 84 is near or adjacent to the cylindrical portion 82. The seating surface 84 is sized and shaped for slidable mating and eventual frictional engagement with the retainer 12, as described more fully below. The cavity 80 opens into the U-shaped channel 44 and also to a lower neck 86 defining a bore or circular opening that communicates with a lower exterior 88 of the base 40. The circular neck 86 is coaxially aligned with the rotational axis B of the receiver 10. The neck 86 is sized and shaped to be smaller than an outer radial dimension of the open, uncompressed retainer 12, as will be discussed further below, so as to form a restriction at the location of the neck relative to the retainer 12, to prevent the uncompressed retainer 12 from passing from the cavity 80 and out to the lower exterior 88 of the receiver 10 when the retainer 12 is seated and loaded.

With reference to FIGS. 1, 3, 4 and 8-10, the partially spherical and discontinuous or open retainer 12 that both retains and articulates is used to hold the spherically surfaced 30 upper portion 8 of the shank 4 within the receiver 10 and is also independently slidably and pivotally engageable with both the shank upper portion 8 at the surface 30 and the receiver 10 at the seating surface 84. The retainer 12 has an operational central axis C that may be the same or different from the axis A associated with the shank 4, or the axis B associated with the receiver 10 when the shank upper portion 8 and the retainer 12 are installed within the receiver 10. The retainer 12 has a central channel or through bore substantially defined by a discontinuous inner partially spherical surface 90. The surface 90 extends from a substantially planar annular top 92 to an inner neck 94 disposed near a substantially planar annular bottom surface 96. An inner chamfer 98 runs between the neck 94 and the bottom surface 96. The inner spherical surface 90 has a radius sized and shaped to cooperate with a radius of the substantially spherical surface 30 of the shank upper portion 8 such that the surface 90 slidingly and pivotally mates with the spherical surface 30. The surface 90 may include a roughening or surface finish to aid in frictional contact between the surface 90 and the surface 30, once a desired angle of articulation of the shank 4 with respect to the retainer 12 and also with respect to the receiver 10 is reached.

The resilient retainer 12 includes first and second end surfaces, 100 and 101 disposed in spaced relation to one another and a discontinuous outer partially spherically shaped surface 102. Both end surfaces 100 and 101 are disposed substantially perpendicular to the top surface 92 and the bottom surface 96. A width of the space between the surfaces 100 and 101 is determined to provide adequate space for the retainer 12 to be pinched, with the surfaces 100 and 101 compressed toward one another to an almost touching or touching configuration, to an extent that the compressed retainer 12 is up or bottom loadable into the receiver cavity 80 being received within the lower neck 86 opening of the receiver 10 while mounted on the neck 26 of the bone screw shank body 6. After passing through the bore defined by the lower neck 86 of the receiver 10 simultaneously with the shank upper portion 8, the retainer 12 expands or springs back to an original uncompressed, rounded or collar-like configuration of FIG. 1 once in the cavity 80. The retainer 12 is then expanded about the shank upper portion spherical surface 30 as will be described in greater detail below. Then, once the resilient structure 12 returns to an original form, but now surrounding the spherical structure 30, the engaged structures 8 and 12 are movable together within the cavity 80 at the spherical seat 84 to a variety of positions in which the surface 102 of the retainer 12 is in slidable mating engagement with the seating surface 84 of the receiver 10.

Figures 23, 24, 25:
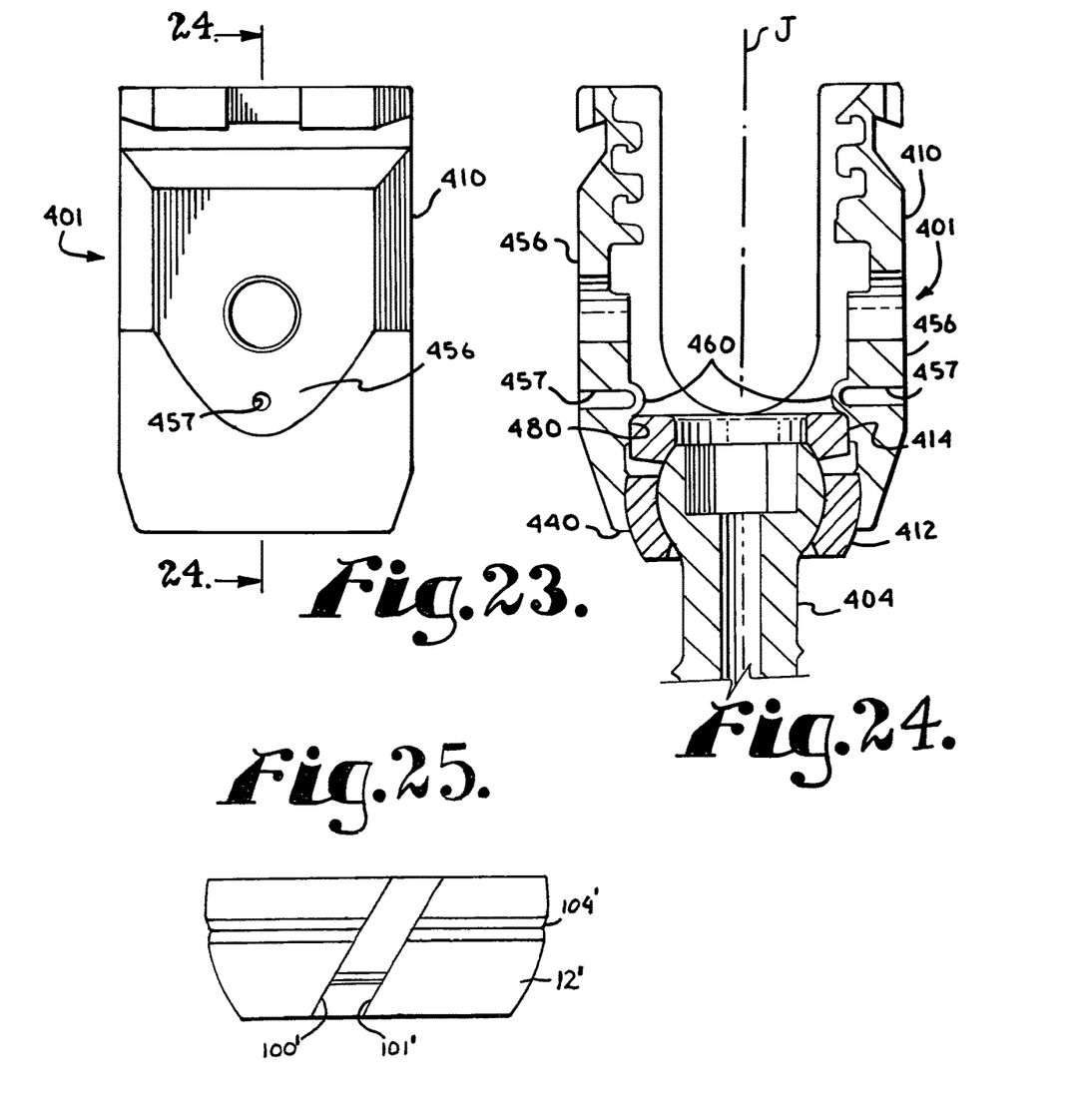
FIG. 23 is an enlarged and partial side elevational view of a fourth embodiment of a bone screw assembly according to the invention.
FIG. 24 is an enlarged and partial cross-sectional view taken along the line 24-24 of FIG. 23 showing a shank, a retainer, a compression insert and a receiver of the assembly of FIG. 23.
FIG. 25 is an enlarged rear elevational view of an alternative embodiment of the retainer of FIG. 1 shown in FIG. 9.

The illustrated embodiment of the retainer 12 shows the surfaces 100 and 101 as substantially parallel and vertical, however, in other embodiments according to the invention, such as the retainer 12' shown in FIG. 25, opposing surfaces 100' and 101' are oriented obliquely or at a slight angle with respect to top and bottom surfaces thereof, advantageously allowing for the surfaces 100' and 101' to slide and ride up upon one another during assembly with the other components of the assembly 1, allowing for greater compression of the retainer 12' without increasing the space between the surfaces 100' and 101' when the retainer 12' is in an uncompressed state. Depending upon the amount of compression desired during loading of the retainer 12' into the receiver 10, the oblique angle may be modified. The retainer 12' is otherwise identical or substantially similar to the retainer 12 in form and function. Furthermore, the illustrated embodiment 12 and 12' include an outer groove 104 and 104', respectively, that may be needed in some instances for clearance within the receiver 10 when the retainer 12 or 12' is expanded about the spherical surface 30 of the shank upper portion 8. Also, other embodiments according to the invention, particularly smaller bone screw assemblies, may include retainers small enough to top load into the receiver channel upper opening 46, rather than loading through the receiver neck 86.

With reference to FIGS. 1, 3 and 4, the compression member or insert 14 is sized and shaped to be received by and uploaded into the receiver 10 at the lower neck 86. In operation, the insert 14 is disposed between the rod 21 and the upper portion 8 of the bone screw 4 as illustrated for example in FIGS. 3 and 4. When the closure structure 18 presses upon the rod 21, the rod 21 operatively presses upon the insert 14 that in turn presses upon the shank upper portion 8 that in turn presses against the retainer 12 that in turn presses against the seating surface 84 of the receiver 10, resulting in ultimate frictional engagement and locking of the angular position of the bone screw shank 4 with respect to the receiver 10. The compression insert 14 has an operational central axis D that is the same as the central axis B of the receiver 10.

Figure 5:
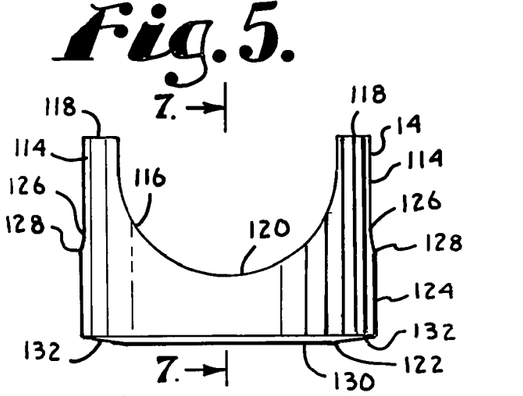
FIG. 5 is an enlarged front elevational view of the compression insert of FIG. 1.
Figures 6, 8, 9, 10:
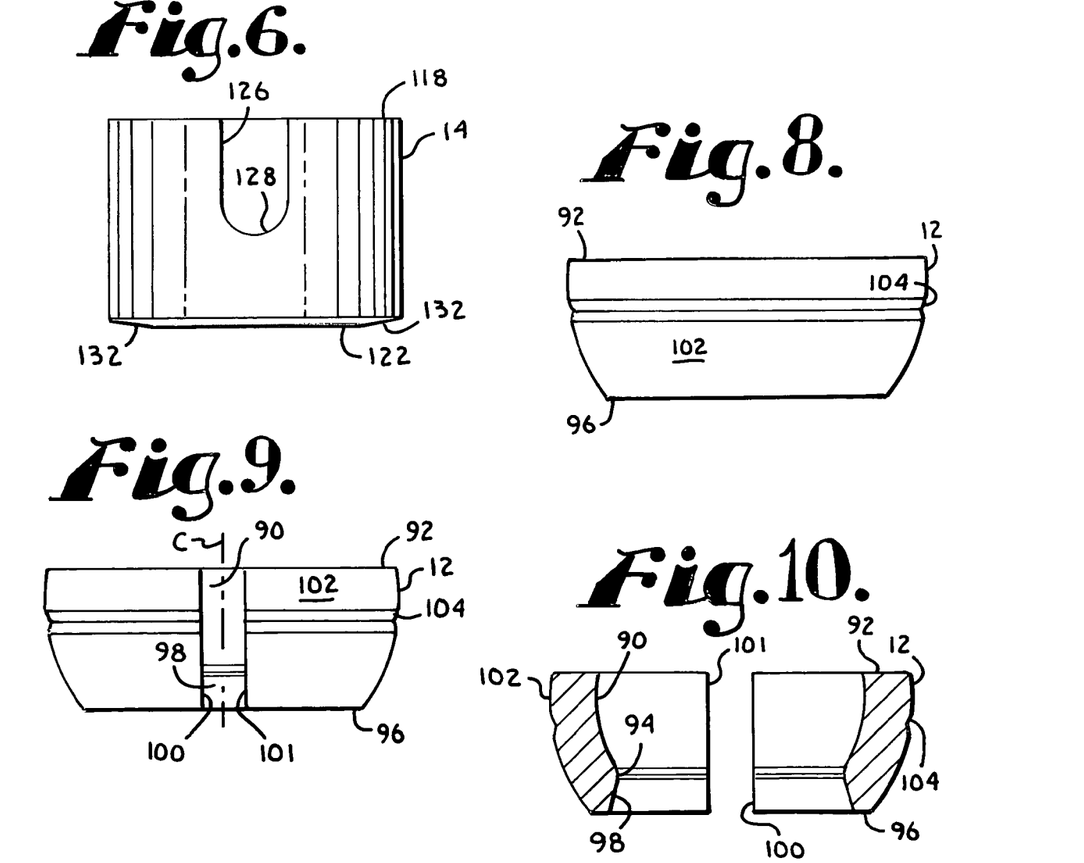
FIG. 6 is an enlarged side elevational view of the compression insert of FIG. 1.
FIG. 8 is an enlarged front elevational view of the retainer of FIG. 1.
FIG. 9 is an enlarged rear elevational view of the retainer of FIG. 1.
FIG. 10 is an enlarged front elevational view, similar to FIG. 8 with portions broken away to show the detail thereof.
Figure 7:
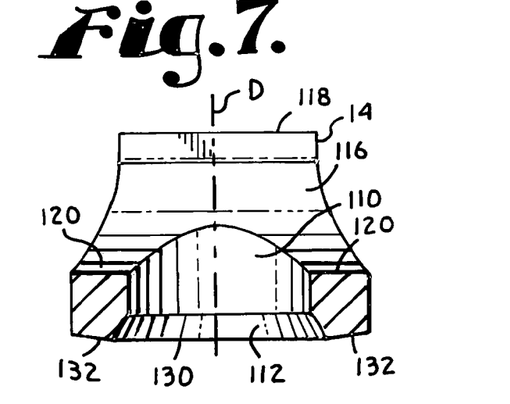
FIG. 7 is a cross-sectional view taken along the line 7-7 of FIG. 5.

With particular reference to FIGS. 5-7, the compression insert 14 has a central channel or through bore substantially defined by a an inner cylindrical surface 110 and an inner partially spherical surface 112, both having the central axis D. The compression insert 14 through bore is sized and shaped to receive a driving tool (not shown) therethrough that engages the shank drive feature 34 when the shank body 6 is driven into bone. The surface 112 is sized and shaped to cooperate with the spherical surface 30 of the shank upper portion 8 such that the surface 112 slidingly and pivotally mates with the spherical surface 30. The surface 112 may include a roughening or surface finish to aid in frictional contact between the surface 112 and the surface 30, once a desired angle of articulation of the shank 4 with respect to the retainer 12 and the receiver 10 is reached.

The compression insert 14 also includes a pair of arms 114 with a U-shaped surface or saddle 116 formed therebetween. The saddle 116 defines a U-shaped channel that communicates with the bore defined by the cylindrical surface 110 and the spherical surface 112. The curved surface or saddle 116 is sized and shaped to closely receive the cylindrical rod 21. With reference to the axis D, the saddle 116 extends from top surfaces 118 of the arms to a curved lower seat 120 near a bottom surface 122 of the insert 114. In operation, the lower seat 129 (as well as a substantial portion of a remainder of the saddle 116) frictionally engages the surface 22 of the rod 21.

A base having a cylindrical surface 124 is disposed between the saddle 116 and the bottom surface 122. The cylindrical surface 124 also extends about the arms 114. Formed in the surface 124 and located centrally with respect to each arm 114 is a shallow groove 126. Each groove 126 is U-shaped and runs from the respective top surface 118 to a curved bottom 128 located approximately centrally between the top surface 118 and the bottom surface 122. The grooves 126 are sized and shaped to cooperate with the tabs 60 of the receiver 10 as will be described in greater detail below. Thus, although the grooves 126 may be of any shape, the grooves 126 preferably are elongate, running parallel to the axis D and have a width that receives the respective tab 60 within such groove. The bottom surface 122 includes a substantially planar and annular central portion 130 disposed perpendicular to the axis D. The bottom portion 130 extends about the bore defined by the inner spherical surface 112. The bottom surface 122 further includes an outer planar and annular surface portion 132 disposed at an angle with respect to the surface portion 130. The surface portion 132 angles upwardly (toward the top surfaces 118) and outwardly (away from the axis D) from the surface 130. As shown in FIG. 3, the surface portion 132 provides clearance for articulated movement of the retainer 12 and the bone screw shank 4.

The compression or pressure insert 14 ultimately seats on the shank upper portion 8 and is disposed substantially in the upper cylindrical portion 82 of the cavity 80, with the tabs 60 holding the insert 14 in desired alignment with respect to the rod 21 as will be described in greater detail below. In operation, the insert 14 extends at least partially in the channel 44 such that the saddle 116 surface substantially contacts and engages the outer surface 22 of the rod 21 when such rod is placed in the receiver 10 and the closure structure or top 18 is tightened therein.

With reference to FIGS. 1 and 4, the closure structure or closure top 18 can be any of a variety of different types of closure structures for use in conjunction with the present invention with suitable mating structure on the upstanding arms 42. In the embodiment shown, the closure top 18 is rotatably received between the spaced arms 42, but could be a slide-in closure structure. The illustrated closure structure 18 is substantially cylindrical and includes an outer helically wound guide and advancement structure 142 in the form of a flange form that operably joins with the guide and advancement structure 52 disposed on the arms 42 of the receiver 10. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 18 downward between the arms 42 and having such a nature as to resist splaying of the arms 42 when the closure structure 18 is advanced into the U-shaped channel 44. The illustrated closure structure 18 also includes a top surface 144 with an internal drive 146 in the form of an aperture that may be a hex drive, or as illustrated, a star-shaped internal drive, for example, sold under the trademark TORX or other internal drives such as slotted, tri-wing, spanner, two or more apertures of various shapes, and the like. A driving tool (not shown) sized and shaped for engagement with the internal drive 146 is used for both rotatable engagement and, if needed, disengagement of the closure 18 from the receiver arms 42. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A bottom surface 148 of the closure may be planar or include a point, points, a rim or roughening for engagement with the surface 22 of the rod 21. The illustrated closure top 18 further includes a cannulation through bore 150 extending along a central axis thereof and through the top surface 144 and the bottom surface 148. Such a through bore provides a passage through the closure 18 interior for a length of wire (not shown) inserted therein to provide a guide for insertion of the closure top into the receiver arms 42.

Prior to the polyaxial bone screw assembly 1 being placed in use according to the invention the tabs 60 of the receiver 10 are preferably bent inwardly toward the axis B as shown in FIGS. 1, 2 and 4. This is accomplished by inserting an elongate tool (not shown) into each of the tooling apertures 54 and pressing the respective tab 60 inwardly toward the axis B until the tab end 64 is disposed at least partially within the upper cylindrical portion 82 of the cavity 80. It is noted that alternatively, in some embodiments according to the invention, the tabs 60 are bent inwardly toward the axis B after the pressure insert 14 is located in the cylindrical portion 82 of the cavity 80. For example, if the insert 14 is top loaded through the opening 46 of the receiver 10, it may be desirable to first load the insert 14 into the receiver, align the grooves 126 with the tabs 60 and then press the tabs 60 until such tabs come into frictional engagement with surfaces of the receiver 14 disposed within the shallow grooves 126.

Also prior to the polyaxial bone screw assembly 1 being placed in use according to the invention, the retainer 12 is first inserted about the neck 26 of the shank body 6 by inserting the shank tip 28 into the retainer 12 through bore defined by the inner surface 90 and feeding the shank body 6 therethrough until the retainer 12 is located at the neck 26. Alternatively, in certain embodiments, the retainer 12 is placed near the neck 26 and the end surfaces 100 and 101 are pulled away from one another and pressed against and about the neck 26 until the surfaces 100 and 101 expand around the neck 26 and then spring back into an original or first position with the inner surface 90 disposed adjacent to the neck 26 and the top surface 92 facing toward the spherical surface 30 of the shank upper portion 8.

In the illustrated embodiment, prior to inserting the shank 4 and connected retainer 12 into the receiver 10, the compression insert 14 is up or bottom loaded into the receiver 10 through the lower neck 86 with the saddle 116 facing the neck 86 and the arms 114 aligned with the tabs 60. The insert 14 is then moved upwardly through the lower seat 84 of the receiver 10 and into the cylindrical portion 82 of the cavity 80. As the insert 14 is moved upwardly into the cylindrical portion 82, each of the tabs 60 are received in a groove 126. The tabs 60 press against the insert 14 at the grooves 126, allowing for some upward and downward adjustment of the insert 14. However, rotation of the insert 14 about the axis B is prohibited by the tabs 60 abutting against surfaces forming the grooves 126. Surfaces defining the lower curved portion 128 of the grooves 126 also prohibit the tabs 60 from sliding along the outer cylindrical surface 124 of the insert 14, thus resisting upward movement of the insert 14 out of the receiver 10.

In certain embodiments, it may be desirable to place the compression insert 14 on the shank upper portion 8 with the spherical surface 112 seated on the surface 30 of the shank upper portion 8 and then upload the insert 14 simultaneously with the shank upper portion 8 and the retainer 12. The upper portion 8 and the connected retainer 12 are simultaneously up or bottom-loaded into the receiver cavity 80 by inserting the upper portion 8 through the lower neck 86 and into the cavity 80 lower seat portion 84 and manually compressing the retainer 12 by pinching the surfaces 100 and 101 toward one another and inserting the neck 26 and the compressed retainer 12 into the bore formed by the lower neck 86 of the receiver 10. After the retainer 12 moves beyond the neck 86, the compressive force is removed and the retainer 12 resiliently springs back and returns to the original ring-like or collar-like orientation, capturing the shank upper portion 8 within the receiver 10. Then, the shank body 6 is pulled downwardly away from the base 40 of the receiver 10, forcing the retainer 12 to temporarily expand as the retainer 12 moves along the spherical surface 30 of the shank upper portion 8 with the end surfaces 100 and 101 moving away from one another. Such an expansion of the retainer 12 allows the spherical surface 30 to slide or snap into the retainer 12 with the spherical surfaces 30 and 90 becoming aligned and the shank upper portion 8 ultimately in sliding cooperation with the inner surface 90 of the retainer 12. The retainer 12 thus resiliently returns to the original ring-link orientation, with the spherical surface 90 capturing the shank upper portion 8 at the spherical surface 30, but allowing for pivotal movement or articulation of the shank upper portion 8 with respect to the retainer 12. Once the retainer 12 returns to the original orientation, both the connected structures 8 and 12 drop down to a seated position at the spherical surface 84 of the receiver 10, with the retainer 12 being independently slidable with respect to both the shank upper portion 8 and the receiver 10, forming a multi- or compound articulation or joint between the shank 4 and the receiver 10. The compression insert 14 may then be pressed downwardly and into full contact with the surface 30.

The retainer 12 and the attached shank upper portion 8 may then be manipulated into a substantially coaxial position with the insert 14 in readiness for bone implantation. The assembly 1 is typically screwed into a bone, such as a vertebra (not shown), by rotation of the shank 4 using a driving tool (not shown) that operably drives and rotates the shank 4 by engagement thereof with the drive feature 34.

Typically, the receiver 10, the compression or pressure insert 14, and the retainer 12 are assembled on the shank 4 before inserting the shank body 6 into a vertebra. However, in certain circumstances, such as when a small bone screw is utilized and the retainer is top loadable, the shank body 6 can be first partially implanted with the shank upper portion 8 extending proud to allow assembly with the receiver 10, followed by assembly with a top loaded retainer 12 and a top loaded compression insert 14. Then the shank body 6 can be further driven into the vertebra.

The vertebra (not shown) may be pre-drilled to minimize stressing the bone and have a guide wire (not shown) inserted to provide a guide for the placement and angle of the shank 4 with respect to the vertebra. A further tap hole may be made using a tap with the guide wire as a guide. Then, the bone screw assembly 1 or the solitary shank 4, is threaded onto the guide wire utilizing the cannulation bore 35 by first threading the wire into the opening at the bottom 28 and then out of the top opening at the drive feature 34. The shank 4 is then driven into the vertebra using the wire as a placement guide. It is foreseen that the bone screw assemblies 1, the rod 21 (also having a central lumen in some embodiments) and the closure top 18 can be inserted in a percutaneous or minimally invasive surgical manner, utilizing guide wires.

With reference to FIG. 4, the rod 21 is eventually positioned in an open or percutaneous manner in cooperation with the at least two bone screw assemblies 1. Alignment of the rod surface 22 with the saddle 116 of the insert 14 is initially provided and then maintained by pressure placed at the insert grooves 126 by the tabs 60. A closure structure 18 is then inserted into and advanced between the arms 42 of each of the bone screw assemblies 1. The closure structure 18 is rotated, using a tool engaged with the inner drive 146 until a selected pressure is reached at which point the rod 21 engages the saddle 116 and the rod is urged toward, but not in contact with the lower seat 48 of the receiver 10 that defines the U-shaped channel 44. For example, about 80 to about 120 inch pounds pressure may be required for fixing each bone screw shank 7 with respect to the receiver 10.

As each closure structure 18 rotates and moves downwardly into the respective receiver 10, the bottom surface 148 presses against the rod surface 22, biasing the rod into engagement with the compression insert 14 that operably produces a frictional engagement between the insert surface 112 and the shank surface 30 and also urges the shank upper portion 8 toward the retainer 12 and, in turn, the structure 12 in a direction toward the base 40 of the receiver 10, so as to frictionally seat the spherical surface 30 against the inner spherical surface 90 of the retainer 12 and the outer spherical surface 102 of the retainer 12 against the internal spherical seating surface 84 of the receiver 10, also fixing the shank 4 and the retainer 12 in a selected, rigid position relative to the receiver 10. At this time it is also possible for the retainer 12 to expand somewhat for an even tighter fit in the receiver cavity lower seat 84.

If removal of the rod 21 from any of the bone screw assemblies 1 is necessary, or if it is desired to release the rod 21 at a particular location, disassembly is accomplished by using the driving tool (not shown) that mates with the internal drive 146 on the closure structure 18 to rotate and remove the closure structure 18 from the cooperating receiver 10. Disassembly is then accomplished in reverse order to the procedure described previously herein for assembly.

With reference to FIGS. 11-14, an alternative bone screw assembly of the invention, generally 201 includes a shank 204 that further includes a body 206 integral with an upper portion or capture structure 208; a head or receiver 210; a retainer 212 illustrated as an open collar-like retaining and articulating structure; and a compression insert 214. The shank 204, the retainer 212 and the insert 214 are identical or substantially similar to the respective shank 4, retainer 12 and insert 14 previously described herein. The assembly 201 also cooperates with the rod 221 and a closure top 218 that are the same or similar to the respective rod 21 and closure top 18 previously described herein. The receiver 210 is substantially similar to the receiver 10 with the exception of the orientation of spring tabs 260 that are otherwise substantially similar to the tabs 60 previously described herein with respect to the assembly 1. Similar to the previous discussion with respect to the assembly 1, the tabs 260 of the receiver 210, like the tabs 60 of the receiver 10, press against shallow grooves formed on an outside surface of the insert 214, keeping a saddle or curved surface of the insert 212 in a desired alignment to receive and ultimately frictionally engage the rod 221 along a substantial surface of the saddle. The insert may also have a flat outer surface instead of shallow grooves.

Because the illustrated assembly 201 only differs from the assembly 1 with respect to the tabs 260 of the receiver 210, only relevant portions of the receiver 210 will be described in greater detail here: The receiver 210 includes a base 240 integral with a pair of opposed upstanding arms 242 forming a cradle and defining a U-shaped channel 244 between the arms 242 with an upper opening 246 and a lower seat 248, the channel 244 having a width for receiving the rod 221, for operably receiving the rod 221 between the arms 242. Each of the arms 242 has an interior surface 250 that defines the inner cylindrical profile disposed about a central axis G and includes a partial helically wound guide and advancement structure 252. In the illustrated embodiment, the guide and advancement structure 252 is a partial helically wound interlocking flangeform configured to mate under rotation with a similar structure on the closure structure 218. However, it is foreseen that the guide and advancement structure 252 could alternatively be a square-shaped thread, a buttress thread, a reverse angle thread or other thread like or non-thread like helically wound discontinuous advancement structure for operably guiding under rotation and advancing the closure structure 218 downward between the arms 242, as well as eventual torquing when the closure structure 218 abuts against the rod 221.

Figure 11:
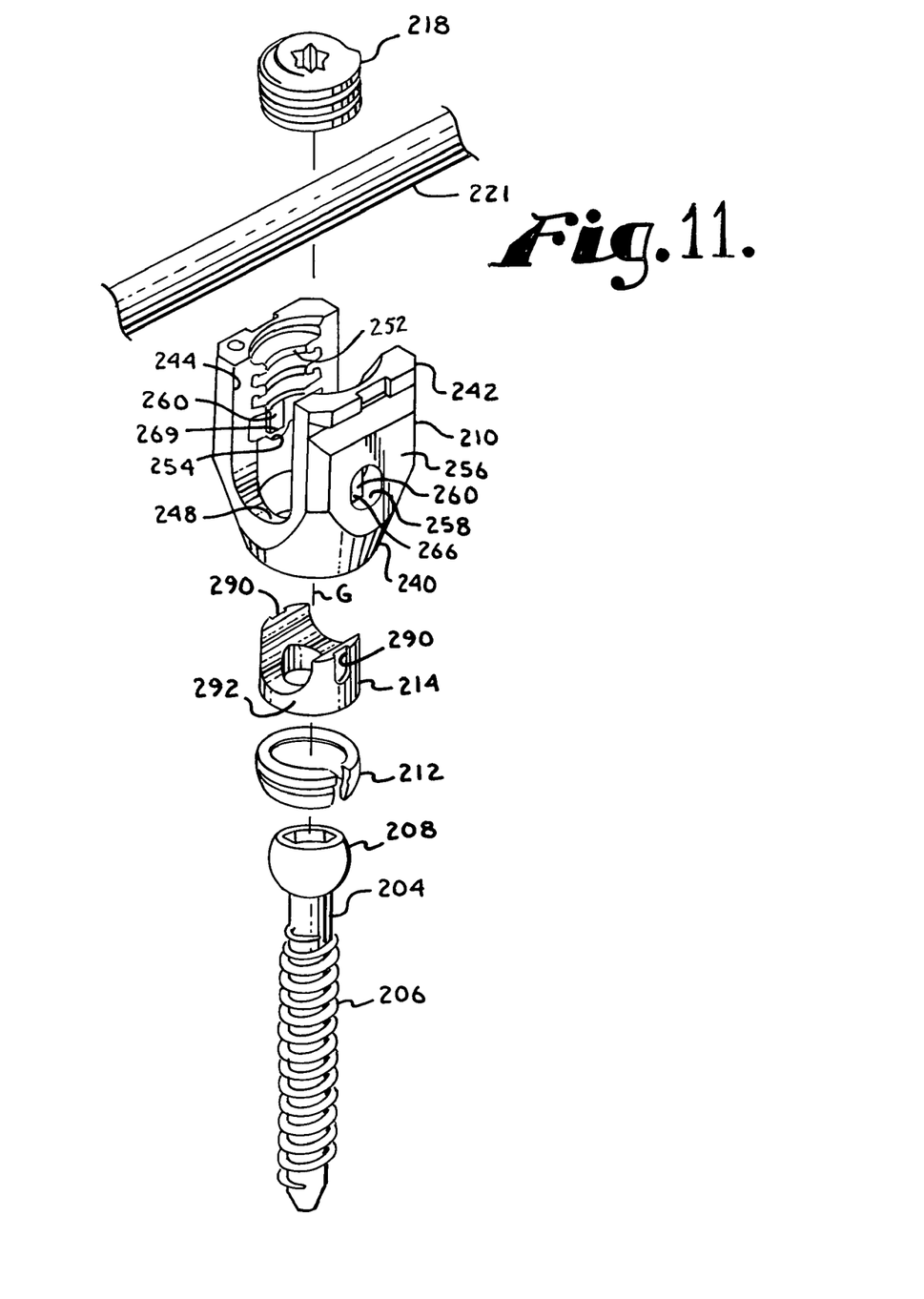
FIG. 11 is an enlarged exploded perspective view of a second embodiment of a bone screw assembly according to the invention including a shank, a retainer, a compression insert and a receiver and shown with a cooperating longitudinal connecting member and a cooperating closure top.
Figures 12, 13, 14:
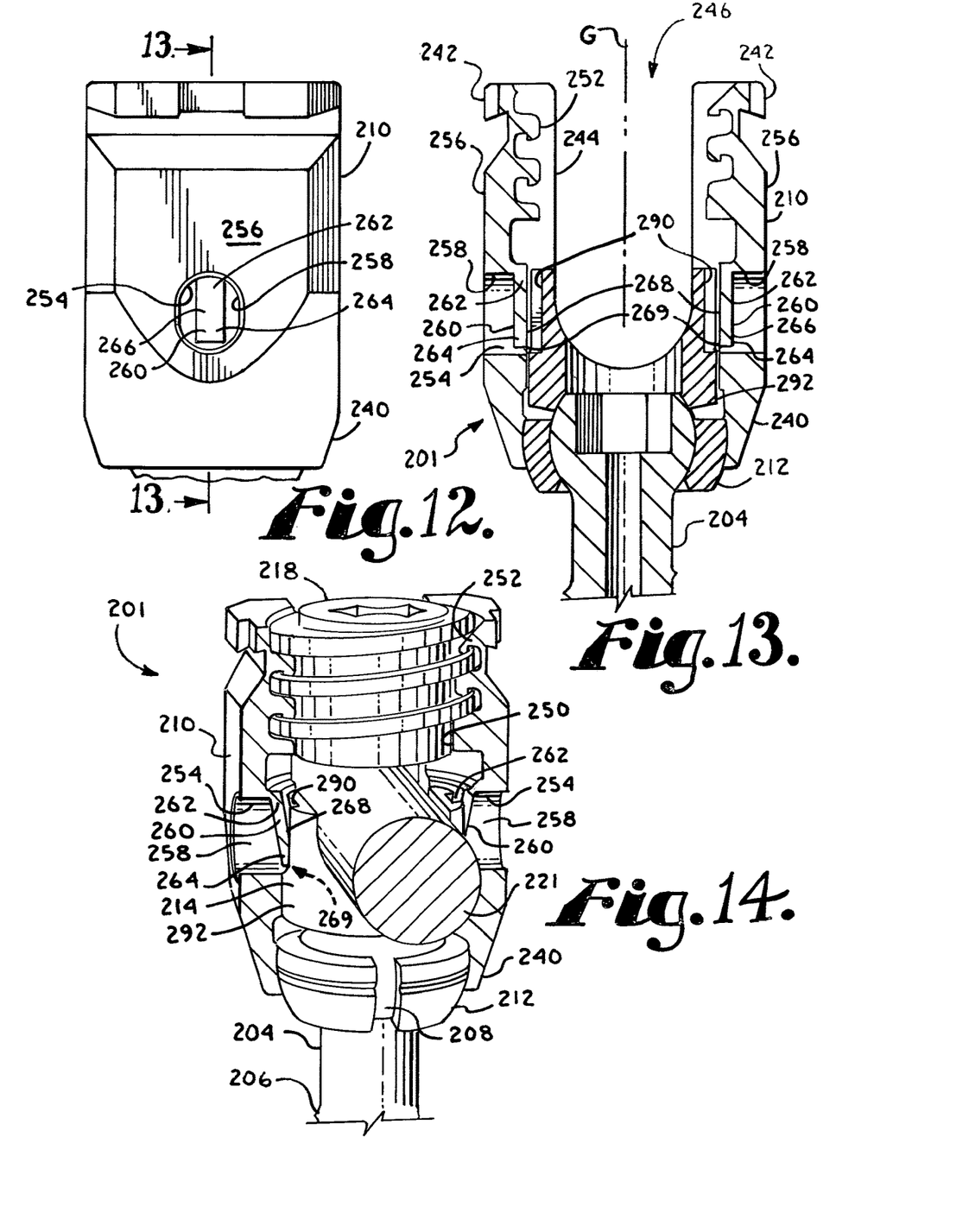
FIG. 12 is an enlarged and partial side elevational view of the bone screw assembly of FIG. 11.
FIG. 13 is an enlarged and partial cross-sectional view taken along the line 13-13 of FIG. 12.
FIG. 14 is an enlarged and partial perspective view of the bone screw assembly of FIG. 11 with portions broken away to show the detail thereof.
Figure 15:
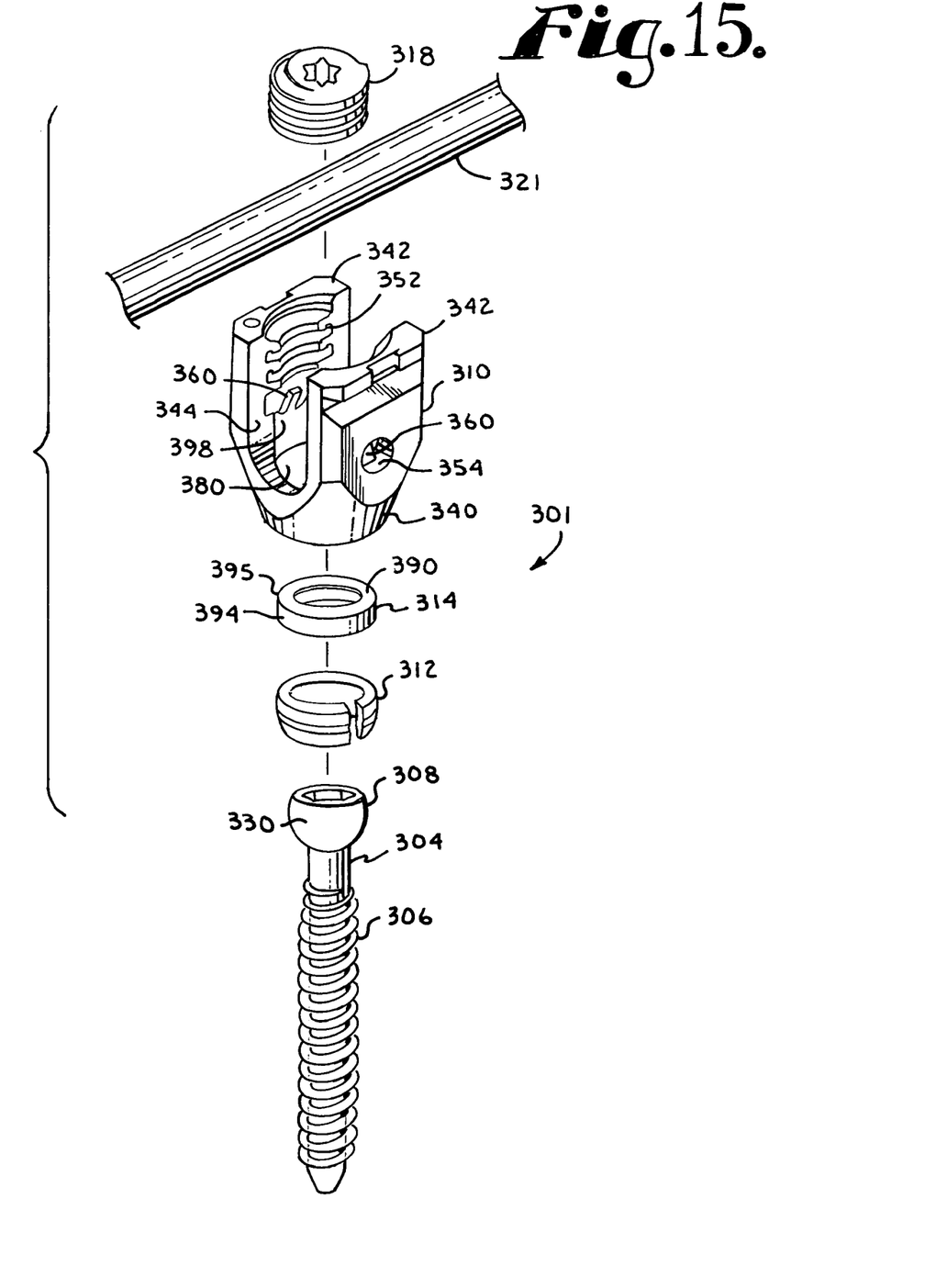
FIG. 15 is an enlarged exploded perspective view of a third embodiment of a bone screw assembly according to the invention including a shank, a retainer, a compression insert and a receiver and shown with a cooperating longitudinal connecting member and a cooperating closure top.

An opposed pair of tool receiving and engaging apertures 254 are formed on outer surfaces 256 of the arms 242. A pair of substantially cylindrical inner surfaces 258 define the apertures 254, with a portion of each of the apertures 254 extending through the arms 242 as best illustrated in FIG. 12. With particular reference to FIGS. 11, 13 and 14, the pair of tabs 260, each having an upper end or body portion 262 integral with a respective arm 242 at an upper portion of one of the cylindrical surfaces 258, and a lower end 264 extending downwardly and eventually inwardly from the respective upper body portion 262 toward the central axis G of the receiver 210. As shown in FIG. 14, an operational orientation of each of the tabs 260 is angled toward the central axis G of the receiver with an inner surface 268 or edge 269 of the lower end 264 in sliding engagement with a slot 290 in the cooperating insert 214. As illustrated in FIGS. 11 and 13, the tabs 260 are typically initially disposed parallel to the central axis of the receiver 210. In the illustrated embodiment, the pressure insert 214, retainer 212 and bone screw shank 204 are first bottom loaded (or may be top loaded) into the receiver 210 in a manner as previously described herein with respect to the assembly 1 and then a tool (not shown) is inserted into each aperture 254 from the outside surface 256 and engages and pushes a surface 266 of the tab 260 and bends the tab 260 inwardly in a direction toward the receiver central axis G until the tab 260 is at the illustrated desired angular position. Such bending of the tabs 260 may also be performed prior to assembly of the receiver 210 with the insert 214, shank 204 and retainer 212. In such an arrangement, the insert 214 may be uploaded or downloaded into the receiver 210 with the saddle portion thereof in alignment with the tabs 260. After the insert 214 is in a desired axial position, the insert 214 is rotated about the axis G with the tabs 260 being manipulated to press against the surface 292. The insert 214 is rotated about the central axis G until the tabs 260 snap into the grooves or depressions 290 (or engage flat surfaces).

It is foreseen that in another embodiment according to the invention, the insert 214 is sized and shaped for top loading into the opening 246 of the receiver 210 and the tabs 260 are bent inwardly toward the axis G prior to assembly of the receiver 210 with the insert 214 and the other bone screw components. During assembly, after the insert 214 is lowered into the receiver 210 and moved past the guide and advancement structure 252, the outer surface 292 presses against the tabs 260, moving the tabs 260 outwardly and away from one another. Then, when the edges 269 of the tabs 260 come into contact with the surface of the grooves 290, the resilient tabs 260 snap into such grooves, maintaining alignment of the insert 214 and resisting any rotational movement of the insert 214 as the insert 214 is lowered into place over the upper portion 208 of the bone screw shank 204.

It is also foreseen that the tabs 260 may be machined or otherwise pre-fabricated to be angled or directed toward the receiver central axis G. As indicated above, the illustrated tabs 260 are resilient, having a spring-like nature. Thus, when operatively cooperating with the insert 214, the tabs 260 bias against the insert 214, holding such insert in a desired position. However, the tabs 260 are flexible enough to allow a user to make desired upward and downward adjustments of the position of the insert 214 within the receiver 210 with respect to the axis G.

With reference to FIGS. 15-21, a third embodiment of a bone screw assembly of the invention, generally 301 includes a shank 304 that further includes a body 306 integral with an upper portion or capture structure 308; a head or receiver 310; a retainer 312 illustrated as an open collar-like retaining and articulating structure; and a compression insert 314. The shank 304, the receiver 310 and the retainer 312 are substantially similar to the respective shank 4, receiver 10 and retainer 12 previously described herein with respect to the assembly 1. The receiver 310 is sized and proportioned slightly differently than the receiver 12 to cooperate with the insert 314. However, the receiver 310 otherwise includes the same component parts previously described herein with respect to the receiver 10. In particular, the receiver 310 includes a central axis H, a base 340, arms 342, a U-shaped channel 344, an interior surface with a guide and advancement structure 352, a pair of opposed apertures 354 upwardly and inwardly extending spring tabs 360, and an inner cavity 380 identical or substantially similar to the respective central axis B, base 40, arms 42, U-shaped channel 44, interior surface with a guide and advancement structure 52, apertures 54, upwardly and inwardly extending spring tabs 60 and inner cavity 80 of the receiver 10 of the assembly 1. The assembly 301 also cooperates with the rod 321 and a closure top 318 that are the same or similar to the respective rod 21 and closure top 18 previously described herein.

The compression or pressure insert 314 functions substantially similarly to the insert 14 previously described herein; however the insert 314 is of a different shape than the insert 14 and thus shall be described in detail herein.

The compression insert 314 is sized and shaped to be received by and uploaded into the receiver 310 at an opening into the cavity 380 at the base 340. In operation, the insert 314 is disposed between the rod 321 and the upper portion 308 of the bone screw shank 304. When the closure structure 318 presses upon the rod 321, the rod operatively presses upon the compression member 314 that in turn presses on the shank upper portion 308, but unlike the assemblies 1 and 101, the member 314 does not include a saddle. Therefore, rotational alignment of the rod 321 with the insert 314 is not necessary. However, because of the compact cylindrical shape of the insert 314, there is a possibility of the insert 314 becoming dislodged from a remainder of the assembly and undesirably moving up into the U-shaped channel 344 and out of the top of the receiver 310. Therefore, the receiver 310 equipped with spring tabs 360 prohibit undesirable upward movement of the insert 314 out of the receiver 310.

Figures 19, 20, 22:
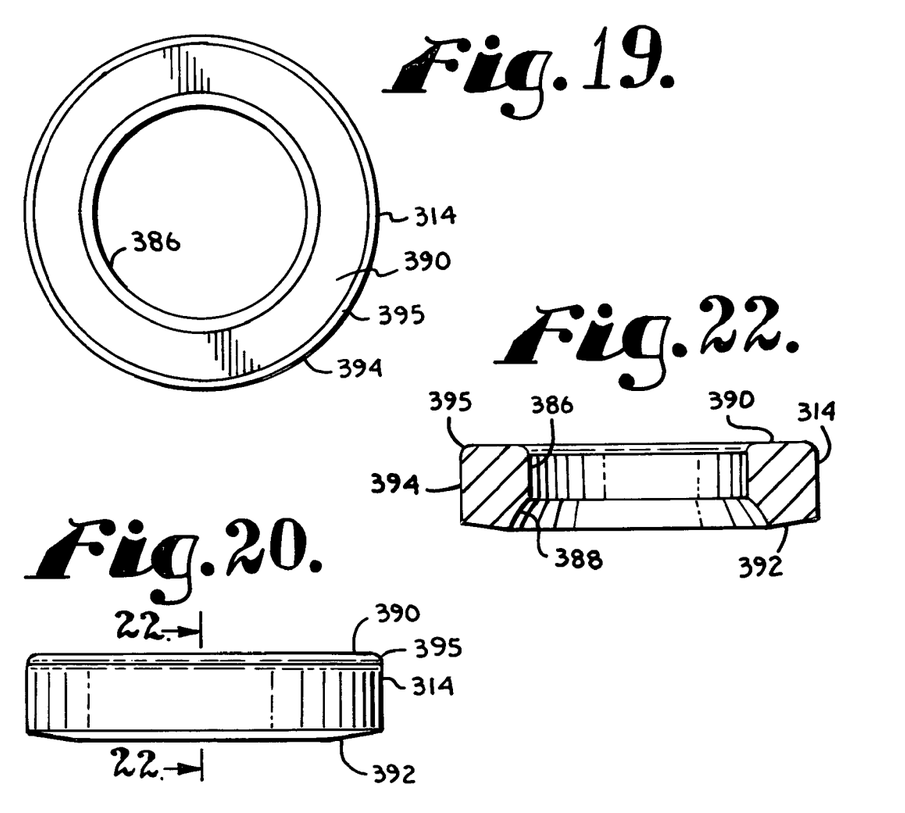
FIG. 19 is an enlarged top plan view of the compression insert of FIG. 15.
FIG. 20 is an enlarged front elevational view of the compression insert of FIG. 15.
FIG. 22 is a cross-sectional view taken along the line 22-22 of FIG. 20.
Figure 21:
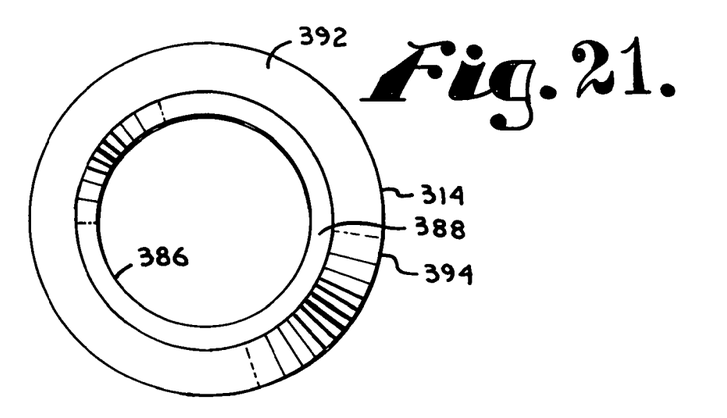
FIG. 21 is an enlarged bottom plan view of the compression insert of FIG. 15.

With particular reference to FIGS. 19-21, the compression insert 314 has an operational central axis that is the same as the central axis H of the receiver 310. The compression insert 314 has a central channel or through bore substantially defined by a an inner cylindrical surface 386 and an inner partially spherical surface 388. The insert through bore is sized and shaped to receive a driving tool (not shown) therethrough that engages a shank internal drive feature formed in the upper portion 308 when the shank is driven into bone. The surface 388 is sized and shaped to cooperate and mate with the spherical surface 330 of the shank upper portion 308 such that the surface 388 slidingly and pivotally mates with the spherical surface 330. The surface 388 may include a roughening or surface finish to aid in frictional contact between the surface 388 and the surface 330, once a desired angle of articulation of the shank 304 with respect to the retainer 312 and the receiver 310 is reached.

Figures 16, 17, 18:
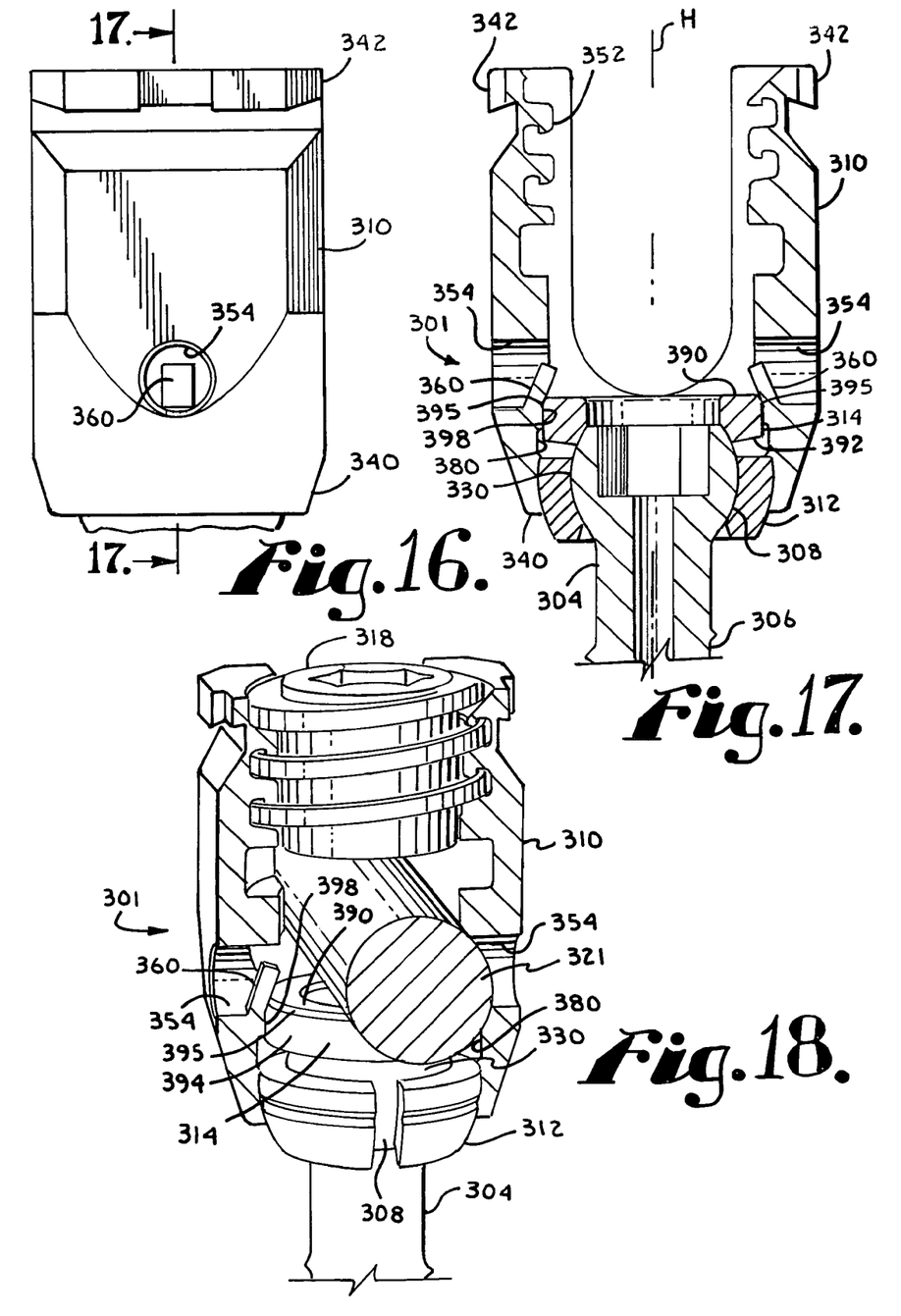
FIG. 16 is an enlarged and partial side elevational view of the bone screw assembly of FIG. 15.
FIG. 17 is an enlarged and partial cross-sectional view taken along the line 17-17 of FIG. 16.
FIG. 18 is an enlarged and partial perspective view of the bone screw assembly of FIG. 15 with portions broken away to show the detail thereof.

The compression insert 314 also includes a substantially planar top surface 390, a bottom surface 392 and an outer cylindrical surface 394. An outer angled surface or chamfer 395 is disposed between and connects the top surface 390 with the outer cylindrical surface 394. The cylindrical surface 394 is sized to be received within the cavity 380 of the receiver 310 and slidingly mate with a cylindrical inner surface 398 partially defining the cavity 380. The inner surface 398 is disposed directly below and adjacent to the spring tabs 360. Thus, the compression insert 314 ultimately seats on the shank upper portion 308 and is disposed at least partially in the channel 344 such that the compression insert 314 top surface 390 substantially contacts the rod 321 when the rod is placed in the receiver 310 and the closure structure 318 is tightened therein. With particular reference to FIG. 17, similar to the bottom surface 132 of the previously described insert 14, the bottom surface 392 of the insert 314 is sloped or angled to provide clearance for pivoting movement of the shank upper portion 308 and the retainer 312.

In operation, the tabs 360 may be bent inwardly toward the axis H before or after insertion of the insert 314 into the cavity 380, either by top or bottom loading. Preferably, the tabs 360 are initially bent inwardly toward the axis H, followed by bottom loading of the insert 314 into the cavity 380 at the cavity opening at the base 340. The shank 304 and the retainer 312 are then bottom loaded in a manner similar to what has been previously described herein with respect to the assembly 1. As best illustrated in FIG. 18, the tabs 360 engage the insert 314 at or near the chamfer 395, prohibiting further upward movement of the insert 314 into a remainder of the cavity 380. Eventually, the rod 321 and the closure top 318 are assembled with the receiver 310 in the manner described previously herein with respect to the receiver 10, rod 21 and closure top 18.

With reference to FIGS. 23 and 24, in a fourth embodiment according to the invention, generally 401, a receiver 410 is substantially identical to the receiver 310 of the assembly 301 with the exception that the spring tabs 360 are removed and replaced with a deformable material portion 460. The assembly 401 otherwise includes a shank 404, a retainer 412 and a compression insert 414 identical or substantially similar to the shank 304, retainer 312 and compression insert 314 previously described herein with respect to the assembly 301. Formed on outside surfaces 456 of the receiver 410 are a pair of opposed apertures 457. Each deformable portion or wall 460 partially defines the respective aperture 457. A tool (not shown) is inserted into the aperture and is pressed against the deformable portion 460, causing the portion 460 to extend into a cavity 480 of the receiver 410 in a direction towards a central axis J. Similar to the spring tabs 360, the now deformed wall portions 460 abut against and prohibit upward movement of the insert 414 and thus desirably retain the insert 414 in the cavity 480. If, as illustrated, the insert 414 is uploadable into the cavity 480 from an opening in the base 440 thereof, the portions 480 are preferably deformed prior to insertion of the insert 414 into the receiver 410. It is foreseen that in downloaded embodiments, the portions 480 may be deformed after downloading of the insert 414 into the cavity 480.

It is to be understood that while certain forms of the present invention have been illustrated and described herein, it is not to be limited to the specific forms or arrangement of parts described and shown.

What is claimed is:

1. A polyaxial bone screw assembly for receiving a spinal rod, the polyaxial screw assembly comprising:
    a shank for anchoring the polyaxial bone screw assembly in bone;
    a receiver comprising a first channel for receiving the spinal rod;
    a retainer including a slit extending through a top surface and a bottom surface, wherein the slit is disposed at an oblique angle relative to the top surface and the bottom surface;
    a compression insert disposable in the receiver, the compression insert having a rod seat for contacting the spinal rod and a mating surface that pivotally mates with the shank; and
    a closure structure insertable into the receiver, the closure structure configured for urging the spinal rod into engagement with the compression insert thereby urging the compression insert into engagement with the shank,
    wherein the polyaxial screw assembly has:
        an unlocked position in which the receiver pivots with respect to the shank and the retainer pivots with respect to both the receiver and the shank, and
        a locked position in which the receiver, retainer, and shank are locked in motion relative to each other.

2. The polyaxial bone screw assembly of claim 1, wherein the receiver includes a pair of opposed receiver arms defining the first channel for receiving the spinal rod; and
    wherein the compression insert includes a pair of opposed insert arms extending upwards and flanking the rod seat.

3. The polyaxial bone screw assembly of claim 2, wherein the opposed insert arms define a second channel that aligns with the first channel to receive the spinal rod.

4. The polyaxial bone screw assembly of claim 3, wherein the compression insert is top loadable into the receiver with the second channel misaligned from the first channel and then rotatable into a position with the second channel aligned with the first channel.

5. The polyaxial bone screw assembly of claim 1, wherein the compression insert has at least one depression formed therein and the receiver has at least one resilient structure extending therefrom, the resilient structure biasing against the compression insert at the depression.

6. The polyaxial bone screw assembly of claim 5, wherein the at least one resilient structure is a pair of opposed spring tabs integral with the receiver and extending toward a central axis of the receiver.

7. The polyaxial bone screw assembly of claim 1, wherein the retainer includes a first end and a second end, the retainer being compressible and expandable with the first end and second end being movable toward and away from one another.

8. The polyaxial bone screw assembly of claim 1, wherein the oblique angle relative to the top and bottom surfaces is configured to cause the surfaces of the retainer on either side of the slit to slide and ride up on one another during assembly with other components, thereby allowing for greater compression of the retainer without increasing the space between the surfaces of the retainer on either side of the slit when the retainer is in an uncompressed state.

9. The polyaxial bone screw assembly of claim 1, wherein the shank is cannulated.

10. The polyaxial bone screw assembly of claim 1, wherein when the compression insert is urged into frictional engagement with the shank, the shank is urged into frictional engagement with the retainer and the retainer is urged into frictional engagement with the receiver.

11. The polyaxial bone screw assembly of claim 10,
wherein the receiver includes a pair of opposed receiver arms defining the first channel for receiving the spinal rod, and
wherein the pair of opposed receiver arms include engagement features formed thereon to cooperatively engage the closure structure.

12. The polyaxial bone screw assembly of claim 11, wherein the engagement features are situated on inner surfaces of the opposed receiver arms.

13. The polyaxial bone screw assembly of claim 1,
wherein the retainer comprises an upper surface, a lower surface, an outer surface, and an inner surface,
the outer surface being spherical and in articulating engagement with an inner spherical surface of the receiver, and
the inner surface being spherical up to the upper surface and in articulating engagement with a spherical outer surface of an upper portion of the shank.

14. The polyaxial bone screw assembly of claim 1, wherein:
the receiver defines a curved seat in which a curved outer portion of the retainer is configured to pivot; and
the retainer defines an inner surface having a radius sized and shaped to cooperate with the shank to form a pivoting relationship between the retainer and the shank, thereby configuring the retainer to pivot with respect to both the receiver and the shank.

15. A polyaxial bone screw assembly for receiving a spinal rod, the polyaxial bone screw assembly comprising:
a shank for anchoring the polyaxial bone screw assembly in bone;
a receiver comprising a first channel for receiving the spinal rod;
a retainer, wherein the retainer defines an outer groove configured to provide clearance when the retainer is disposed within the receiver and when the retainer is expanded about a spherical surface the shank;
a compression insert disposable in the receiver, the compression insert having a rod seat for contacting the spinal rod and a mating surface that pivotally mates with the shank; and
a closure structure insertable into the receiver, the closure structure configured for urging the spinal rod into engagement with the compression insert thereby urging the compression insert into engagement with the shank,
wherein the polyaxial screw assembly has:
an unlocked position in which the receiver pivots with respect to the shank and the retainer pivots with respect to both the receiver and the shank, and
a locked position in which the receiver, retainer, and shank are locked in motion relative to each other.

16. The polyaxial bone screw assembly of claim 1, wherein an outer portion of the retainer is spherical segmental in shape.

17. The polyaxial bone screw assembly of claim 15, wherein:
the receiver defines a curved seat in which a curved outer portion of the retainer is configured to pivot; and
the retainer defines an inner surface having a radius sized and shaped to cooperate with the shank to form a pivoting relationship between the retainer and the shank, thereby configuring the retainer to pivot with respect to both the receiver and the shank.

18. The polyaxial bone screw assembly of claim 15, wherein the retainer includes a first end and a second end, the retainer being compressible and expandable with the first end and second end being movable toward and away from one another.

19. A The polyaxial bone screw assembly for receiving a spinal rod, the polyaxial bone screw assembly comprising:
a shank for anchoring the polyaxial bone screw assembly in bone;
a receiver comprising a first channel for receiving the spinal rod;
a retainer, wherein the retainer defines: a planar annular top; a bottom surface; an inner neck; a curved surface between the planar annular top and the inner neck; and an inner chamfer running between the inner neck and the bottom surface;
a compression insert disposable in the receiver, the compression insert having a rod seat for contacting the spinal rod and a mating surface that pivotally mates with the shank; and
a closure structure insertable into the receiver, the closure structure configured for urging the spinal rod into engagement with the compression insert thereby urging the compression insert into engagement with the shank,
wherein the polyaxial screw assembly has:
an unlocked position in which the receiver pivots with respect to the shank and the retainer pivots with respect to both the receiver and the shank, and
a locked position in which the receiver, retainer, and shank are locked in motion relative to each other.

20. The polyaxial bone screw assembly of claim 19, wherein:
the receiver defines a curved seat in which a curved outer portion of the retainer is configured to pivot; and
the retainer defines an inner surface having a radius sized and shaped to cooperate with the shank to form a pivoting relationship between the retainer and the shank, thereby configuring the retainer to pivot with respect to both the receiver and the shank.

* * * * *